US006868361B2

(12) United States Patent
Desa et al.

(10) Patent No.: US 6,868,361 B2
(45) Date of Patent: Mar. 15, 2005

(54) METHOD OF DETERMINING THE VOLUME SCATTERING FUNCTION OF OCEAN WATERS IN THE BACKWARD DIRECTION USING A SATELLITE OCEAN COLOR SENSOR

(75) Inventors: Elgar Desa, Goa (IN); Ehrlich Desa, Goa (IN); Thayapurath Suresh, Goa (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/628,287

(22) Filed: Jul. 29, 2003

(65) Prior Publication Data

US 2005/0027475 A1 Feb. 3, 2005

(51) Int. Cl.$^7$ .......................... H04B 17/00; G01N 21/47
(52) U.S. Cl. ...................... 702/156; 250/574; 356/435; 73/170.29
(58) Field of Search .............................. 702/156, 179; 250/573, 574; 356/342, 343, 435; 73/170.29, 170.34

(56) References Cited

U.S. PATENT DOCUMENTS 4,416,542 A * 11/1983 Mooradian ................... 356/435
4,614,429 A *  9/1986 Johnson ...................... 356/343

OTHER PUBLICATIONS

Funk, C., "Computer simulation of the performance of advance underwater optical viewing systems", OCEANS, Sep. 1971, vol. 3, p. 74–84 Abstract only.*

Zaneveld–J–R–V., "Remotely sensed reflectance and its dependence on vertical structure: a theoretical derivation", Applied–Optics, vol. 21, No. 22, p. 4146–50, Nov. 15, 1982.*

* cited by examiner

Primary Examiner—Kamini Shah
(74) Attorney, Agent, or Firm—Michael D. Bednarek; Shaw Pittman LLP

(57) ABSTRACT

A method of determining the Volume Scattering Function of Ocean Waters in the backward direction using a Satellite Ocean Color Sensor the said method made to exploit the geometry of the sun-ocean-satellite detector to function as a backscatter system comprising of the sun [1] as a source of radiation, the ocean as the sampling volume [2], and the satellite ocean color sensor [3] as the detector of the back-scattered flux from the ocean emanating from separate ocean pixels arranged on a scan line across the track of the satellite payload and arriving at corresponding pixels on the CCD array detector of the satellite sensor [3]; the output signals from each electronic pixel of the detector is shown to be related to the Volume Scattering Function at a fixed scattering angles ($\psi$) which bears a direct relation to the cosines of the solar incident angle ($\theta_s$) and the angle ($\theta_p$) of the upwelled flux at the ocean surface, the Remotely Sensed Reflectance (Rrs), and the diffuse attenuation coefficient (Kd) thereby resulting in a new product of the Volume Scattering Function at fixed backscattering angles.

11 Claims, 6 Drawing Sheets

Optical geometry of a fixed-angle backscattering sensor

METHOD OF DETERMINING THE VOLUME SCATTERING FUNCTION OF OCEAN WATERS IN THE BACKWARD DIRECTION USING A SATELLITE OCEAN COLOR SENSOR

FIELD OF THE INVENTION

The present invention provides a method and a system for determining Volume Scattering Function in rearward direction of ocean waters using a Satellite Ocean Color Sensor The present invention also provides a method and a sytem for determining spectral components of the volume scattering function for different types of ocean water and thereafter recognize these waters by their optical scattering properties.

BACKGROUND AND PRIOR ART REFERENCES TO THE INVENTION

The remote sensing of ocean color by use of a radiometric sensor on a satellite platform is a widely used technique to determine the concentrations of major seawater constituents in the ocean. These constituents are phytoplankton and their detritus, inorganic suspended material and dissolved organic matter. A remote spectral radiometer on a satellite platform is tuned to receive light at several wavelengths in the visible region and near-infrared portions of the electromagnetic spectrum. They are several pathways by which photons from the sun can enter the 'field-of-view' (FOV) of the satellite sensor after interacting with the ocean surface and the atmosphere.

The pathways are illustrated in FIG. 1. For example path (a) illustrates direct specular reflection of the sun's rays from the ocean surface; path (b) corresponds to direct scattering from the atmosphere alone, while path (c) represents rays that are scattered both by the ocean surface and by the atmosphere. The route followed in dashed path (d) is that taken by upwelling light backscattered by different oceanic layers that ultimately reach the ocean surface [2] and are further attenuated by the intervening atmosphere before arriving at the satellite detector [3]. The radiance component (d) carries useful information on the optical properties that are related to seawater constituents that color the ocean.

Most satellite sensors have the means of orienting the detector so as to avoid or minimize specular reflection of path (a) The atmospheric signal arising from path (b) constitutes nearly 80% of the signal scattered into the satellite detector, and carries useful information about the ocean. There are techniques which have been developed by Gordon &Wang (1994), Gordon (1997), and Gordon & Morel (1983) which deal with the removal of the atmospheric component. This will not be of concern to us here.

Hitherto known devices to measure general-angle scattering meter was by Tyler and Richardson (J. E. Tyler, W. H. Richardson, "Nephelometer for the measurement of volume scattering function in-situ", J. Opt.Soc. Am 48, 354–357 (1958)). The first fixed angle optical backscatter devices were reported by Moore et al (C. A. Moore, R.Honey, D. hancock, S.Damron, and R.Hilbers, Development and use of computerized optical sea-truth instrumentation for LIDEX-82, SRI International Project 3878, Final Rep. 1984), and substantial improvements on these devices undertaken by R. Maffione and D. R. Dana (R. A. Maffione, D. R. Dana, "Instruments and methods for measuring the backwardscattering coefficient of ocean waters," Applied Optics, Vol.36, No.24 pp 6057–6067, 1997) with the purpose of finding the best estimate of the back scattering coefficient ($b_b$) via a measurement of Volume Scattering Function (VSF) at a fixed backscatter angle of 142°. The optical geometry of the backscatter meter developed by Maffione and Dana is illustrated in FIG. 2. The meter consists of built in collimated source of light [a light emitting diode—LED] having a finite divergence and propagated at a fixed refracted angle through a glass window of the instrument casing into surrounding seawater. The sample volume at which backscattering occurs (shown as a shaded area in FIG. 2) is the geometric intersection of the field-of-view [FOV] of the source and detector. The detector is placed adjacent to the source. The backscattered flux that falls within the solid angle cone subtended by the sample volume at the detector will be the signal measured by the detector. The receiver detector is frequency modulated so that it phase locks to only the backscattered flux from the LED source. This electrooptical technique rejects ambient light changes and permits its use in bright sunlight. The backscatter coefficient bb in this meter is computed on the basis of the Integral Mean value Theorem such that there is a fixed scattering angle $\psi^*$ of the VSF function where $b_b = 2\pi.\beta(\psi^*)$. The detected signal is proportional to $\beta$ ($\psi^*$) multiplied by a weighting function W (z;c) which varies with the distance z of the sample volume from the backscatter window (see FIG. 2), and the attenuation coefficient of seawater. Most backscatter devices are deployed from a ship or a boat. There are several known drawbacks to these optical backscatter devices which are identifiable:—

- The small volume from which the backscattered flux originates may not capture a representative distribution of suspended particles in the ocean.
- The detected signal has to calibrated by a separate experiment using a Lambertian target in clean water tank.
- The beam attenuation coefficient [c] of the unknown water needs to be known so as to apply a correction to the measurement of backscattered flux. Further if [c] changes by a large factor, as happens in coastal waters, then the centroid angle ($\psi^*$) at which the volume scattering function is measured will also change by several degrees.

The present invention recognizes that the sun, the ocean and a satellite ocean color sensor constitute the elements of a giant backscatter sensor system in the sky. The source of radiation is the sun (the analogue to this is the light emitting diode as the exciting source of the backscatter meter), the ocean surface is the sample volume which emits backscattered flux from the top layer and all layers below the ocean surface in response to the stimulation provided by the sun's radiation, and the detector in our system is the satellite ocean color sensor which receives the backscattered flux from the ocean (the analogue to this is the single photodiode detector used in the backscatter meter).

The present invention provides the means to interpret the satellite signal in terms of the Volume Scattering Function [VSF] in the backward direction at fixed angles by using the existing geometry of a known sun-ocean-satellite detector system. Our best example is the Ocean Colour Monitor (OCM) on the Indian satellite platform IRS-P4, although the same ideas contained here could be applied to other Ocean Color Sensors namely SeaWiFs on the SeaStar satellite. The OCM operates as a push-broom camera which uses as detector, a charge coupled linear array device (CCD) as a light detector (see FIG. 3). The various pathways of photons (as depicted in FIG. 1) result from reflected and backscattered events in the atmosphere and from within the ocean's interior. These pathways are contained within the cone defined by a field of view of +43°, and a total swath width of ~1420 kms. at sea level as seen by the satellite optics (FIG. 3 again). However, within this large cone, each element of the CCD array views an ocean pixel with infinitesimally narrow cones having fixed look angles and a IGFOV (Instantaneous Ground Field of View) of 360 m×236 m. There are 3730 active elements on the CCD array viewing an equal number of contiguous ocean pixels spanning the swath width of the satellite track. Each scan line in the push broom operation is contiguous with each other. Table 1 summarizes the major features of the OCM sensor as it exists on IRS-P4. The eight spectral channels on OCM have separate collecting optics and separate CCD line array detectors each having their own drive and signal processing electronics.

TABLE 1

Features of OCM Camera (see reference 5)

| Feature | Description |
| --- | --- |
| Orbit | Polar sun synchronous |
| Satellite Altitude | 720 kms |
| Swath | >1420 kms |
| Repeativity | 2 days |
| IGFOV (Ocean pixel) | 360 m × 236 m |
| Spectral Channels (nm) Bands 1–8 | 414.2, 441.4, 485.7, 510.6, 556.4, 669, 768.6, 865.1 |
| Active CCD pixels | 3730 elements |

OBJECTS OF THE PRESENT INVENTION

The main object of the present invention is to provide a method for determining the volume scattering function of ocean waters in the backward direction using a satellite ocean color sensor thus enabling large scale coverage of the scattering.

Another object of the present invention is to demonstrate that geometric anlysis of OCM sensor optics results in an operational algorithm that uses existing satellite products to provide a new way to visualize optical scattering of the ocean surface.

Still another object of the present invention is to demonstrate by example the variation of the VSF function at 490 nm using real satellite data.

Yet another object of the present invention is to show that the form of the operational VSF function can be extended to other visible wavebands of the sateliite ocean colour sensor provided valid data on the other satellite products are available.

In a further object of the present invention, the method provided here could be applied to other Ocean Color sensors as has been done in the data presented in FIG. 6 using the SeaWiFs sensor.

BRIEF DESCRIPTION OF THE ACCOMPANYING DRAWINGS

In the drawings accompanying this specification,

FIG. 1 illustrates the different paths taken by the sun's rays in reaching a satellite detector. This has been describes earlier in the opening paragraph.

FIG. 2 represents the optical geometry of a commercial backscatter instrument. The geometric intersection of the field of view (FOV) of the source (light emitting diode) and the detector shown shaded is the sampling volume from which backscatter radiation emanates. The source and detector are both mounted on an endcap of the instrument.

FIG. 3 represents the satellite sensor system [3] looking down at the ocean surface [2]. The Instantaneous Field of View (IFOV) of an ocean pixel [4] is 360 meters across track and 250 meters along track. The swath W of the satellite is 1420 kms, and the altitude H of the satellite is 720 kms. This produces a cone of half angle (θ) equal to 43 degrees subtended by the swath W at the CCD array detector of the satellite sensor. Individual pixels on the CCD array view water pixels of the above size with infinitesimally small FOV's having near zero divergence angles.

FIG. 4 represents the view seen by a center pixel of the satellite's CCD detector of the looking straight down at an ocean pixel of size 360 m×250 m. The angle of the sun's rays is represented by ($\theta_s$) and the angle of the upwelled flux (*) to the zenith direction that reaches the satellite pixel is shown as ($\theta_p$). The backscattering angle ($\psi$) is the deviation produced in the original solar rays. Note that the upwelled flux is an integrated flux composed of all backscatterd events from different layers in the upper ocean under solar excitation.

SUMMARY OF THE INVENTION

Figure 1:
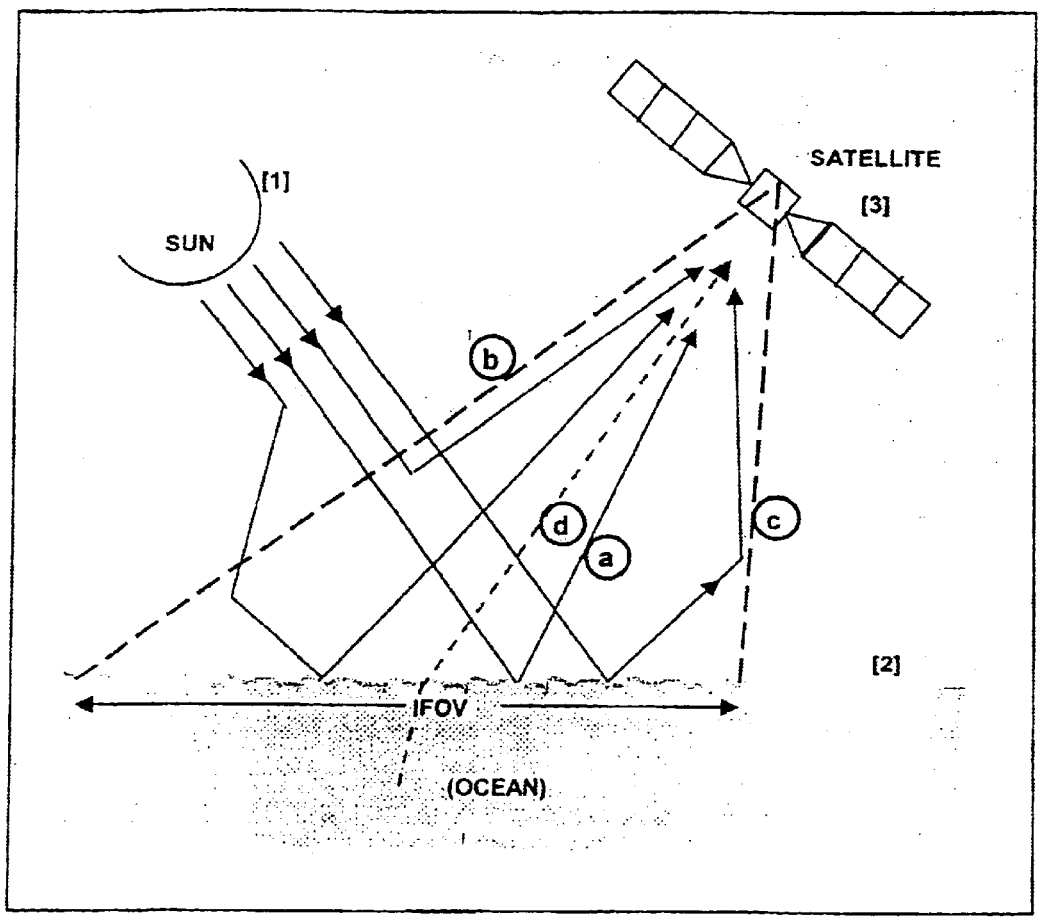
Figure 2:
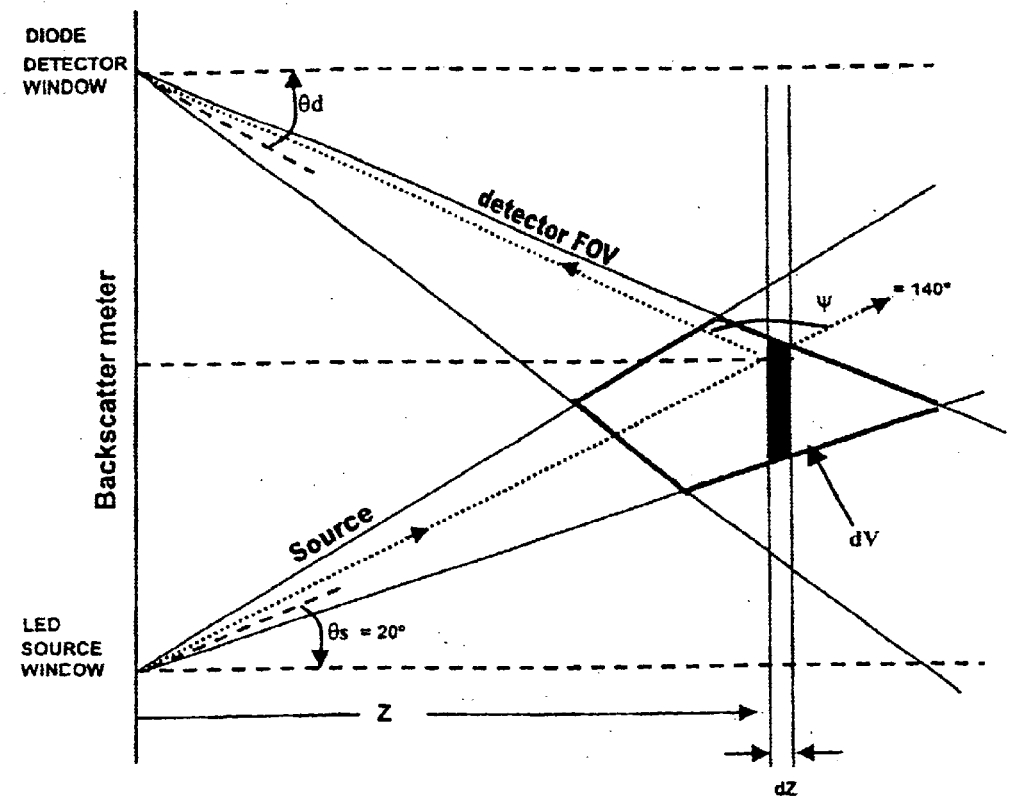

Accordingly, the present invention provides a method of determining the Volume Scattering Function of Ocean Waters in the backward direction using a satellite Ocean Color Sensor. The said method exploits the geometry of the sun-ocean-satellite detector to function as a backscatter system comprising of the sun [1] as a source of radiation, the ocean as the sampling volume [2], and the satellite ocean color sensor [3] as the detector of the backscattered flux from the ocean emanating from separate ocean pixels arranged on a scan line across the track of the satellite payload and arriving at corresponding pixels on the CCD array detector of the satellite sensor [3].

DETAILED DESCRIPTION OF THE PRESENT INVENTION

Accordingly, the present invention provides a method for determining the Volume Scattering Function (VSF) of ocean waters in backward direction using a satellite ocean color sensor, said method comprising the steps of:

(a) obtaining satellite view angle ($\theta_{sat}$), solar angle ($\theta_s$), remote sensed reflectance [Rrs($\theta_p$, λ)] and diffuse attenuation coefficient ($K_d$) at each ocean pixel on a scaline using a satellite ocean color sensor;

(b) calculating corrected look angle of a pixel of satellite ocean color sensor on an ocean pixel using:

$$\theta_p = \theta_{sat} + \sin^{-1}(0.113 \tan \theta_{sat}); \text{ and}$$

(c) calculating the Volume Scattering Function of ocean waters in the backward direction at a given wavelength [β(ψ,λ)] using:

$$\beta(\psi,\lambda) = Rrs(\theta_p,\lambda) K_d [\cos \theta_s \cos \theta_p]$$

In an embodiment of the present invention, the satellite ocean color sensors include CCD array detectors, ocean color monitors and SeaWifs Oocean color sensors.

In another embodiment of the present invention, the detectors view a scan line of ocean pixels arranged along a swath of the ocean surface.

In yet another embodiment of the present invention, the swath "W" of the satellite is about 1420 Kms.

In still another embodiment of the present invention, about 3730 ocean pixels are covered in a satellite scan line.

In one more embodiment of the present invention, wherein Instantaneous Field of View (IFOV) of an ocean pixel about 360 meters across track and about 250 meters along track.

In one another embodiment of the present invention, the Volume Scattering Function of ocean waters in the backward direction is dependent upon the wavelength ($\lambda$).

In a further embodiment of the present invention, the Volume Scattering Function of ocean waters in the backward direction is obtained at a particular wavelength using appropriate wavelength depenedent products of remote sensed reflectance and diffuse attenuation coefficient.

In an embodiment of the present invention, the Volume Scattering Function of ocean waters in the backward direction is obtained at the wavelength of about 490 nm.

In another embodiment of the present invention, the method of interpreting the backscattered flux in terms of the VSF at a fixed wavelength is extendable to all the eight spectral bands of the Oceansat sensor which are located at 410 nm, 443 nm, 490 nm, 510 nm, 555 mm, 670 nm, 785 nm and 865 nm.

In yet another embodiment of the present invention, the method can be extended to contiguous scan lines along the satellite track to generate a high resolution two dimensional volume scattering surface at fixed backscattering angles.

In still another embodiment of the present invention, the method can be extended to create a set of two dimensional volume scattering surfaces in several different visible bands by the satellite ocean color sensor.

Accordingly the present invention provides a method of determining the Volume Scattering Function of Ocean Waters in the backward direction using a satellite Ocean Color Sensor. The said method exploits the geometry of the sun-ocean-satellite detector to function as a backscatter system comprising of the sun [1] as a source of radiation, the ocean as the sampling volume [2], and the satellite ocean color sensor [3] as the detector of the backscattered flux from the ocean emanating from separate ocean pixels arranged on a scan line across the track of the satellite payload and arriving at corresponding pixels on the CCD array detector of the satellite sensor [3]. The Applicants have surprisingly found that the output signals from each electronic pixel of the Ocean Color Sensor is related to the Volume Scattering Function at a fixed scattering angles ($\psi$) which bears a direct relation to the cosines of the solar incident angle ($\theta_s$) and the angle ($\theta_p$) of the upwelled flux at the ocean surface, the Remotely Sensed Reflectance (Rrs), and the diffuse attenuation coefficient (Kd) thereby resulting in a new product of the Volume Scattering Function at fixed backscattering angles.

The method when extended, can result in a more complete spectral characterization of the Volume Scattering Function at eight fixed wavelengths and at 3944 fixed scattering angles determined by the view angles of the detector pixels and the incident solar angle.

The invention is further described in the following examples. The Exampleas are provided to illustrate the present invention and hence, the same should not be construed to limit the scope of the present invention in any manner.

EXAMPLE 1

CALCULATING THE SHARPNESS OF THE FIELD OF VIEW (FOV) CONE ANGLE SUBTENDED BY AN OCEAN PIXEL AT THE SATELLITE DETECTOR PIXELS

This one-time calculation demonstrates that the FOV subtended by a pixel on the ocean surface is extremely narrow, thus simplifying the method of computing the backward VSF by space sensors. Using the parameters in Table 1, we assume an ocean pixel of area 360 m×236 m and a satellite altitude of 720 kms. The solid angle subtended by an off-centre ocean pixel of area 360 m×236 m at the satellite detector height H (=720 kms) is given by:

$$d\Omega = [360 \times 236 \cos \theta_p]/[H^2] \qquad [1]$$

Calculation shows that the solid angles are of the order of <=2.5 mrads for look angles $\theta_p$ in the range +43° to −43. These are extremely narrow FOV angles, and it is safe to assume that the pixel cone can be replaced by a straight line from the centroid of the ocean pixel to the CCD pixel on the satellite detector.

EXAMPLE 2

Figure 3:
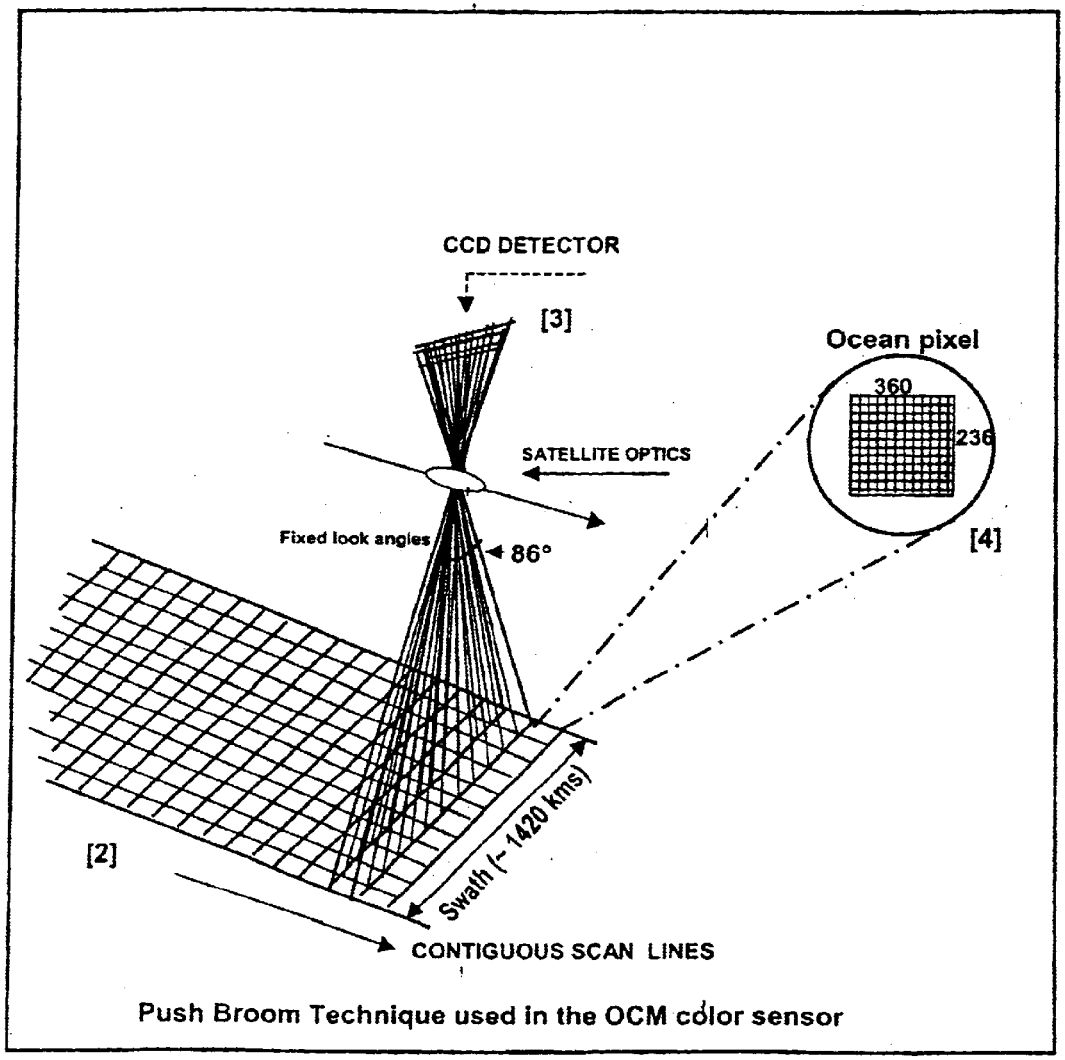
Figure 4:
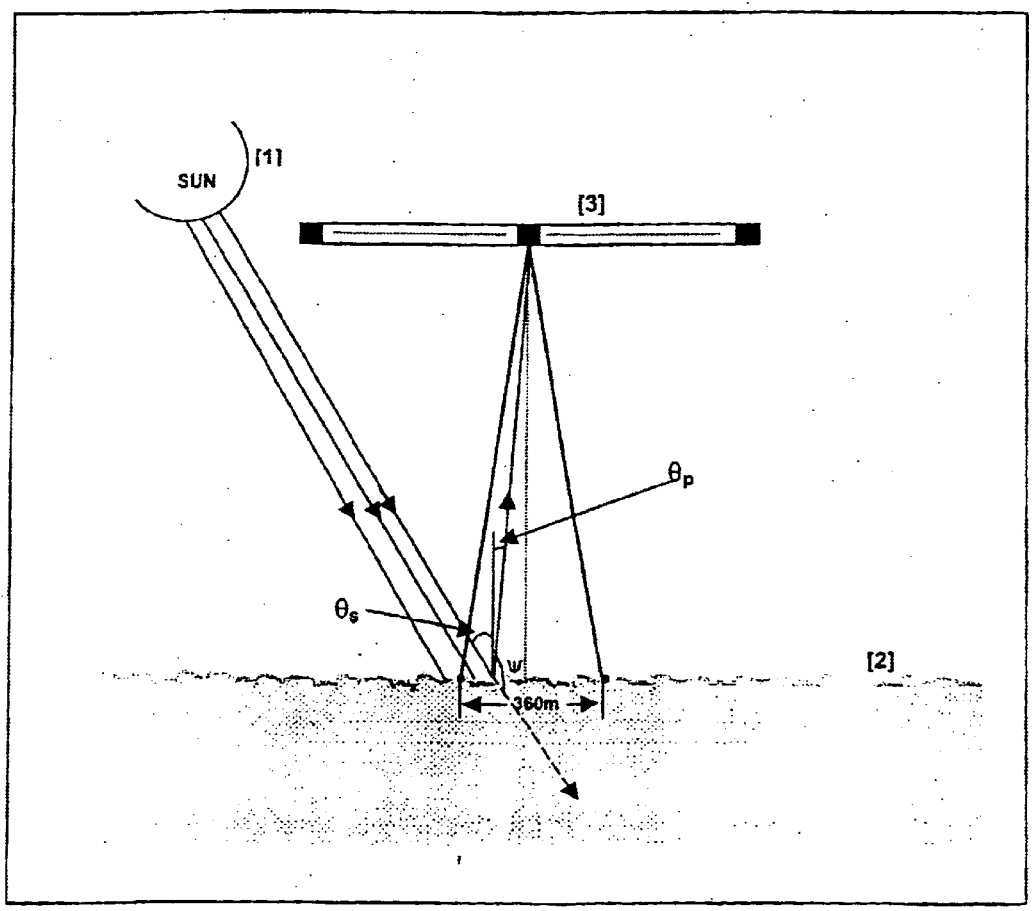

CALCULATING THE SCATTERING ANGLE $\psi$ OF THE BACKWARD VOLUME SCATTERING FUNCTION $\beta(\psi,\lambda)$ AT A GIVEN WAVELENGTH The OCM sensor on the IRS-P4 satellite consists of eight CCD line array detectors, each of which view the backscattered radiation in the eight wavebands shown in Table 1. At any given instant of time, the CCD pixels on a detector view a scan line of ocean pixels arranged along a 1420 km swath of the ocean surface as shown in FIG. 3. Each of the 3730 CCD detector pixels is associated with a look angle $\theta_p$, which have values lying in the range +43° of the fan shaped cone shown in FIG. 3. Simple geometric anaysis of the representation in FIG. 4 shows that the scattering angle $\psi$ can be defined as the angle between the extended solar ray direction and the direction of the backscattered water leaving radiance emerging at the look angle $\theta_p$ to the zenith direction by:

$$\psi = [180 - (\theta_p + \theta_s)] \qquad [2]$$

Given the simple geometric relation in [2], and assuming $\theta_s \sim 17°$ as a typical solar angle shows that $\psi$ will vary over the range 127° to 154° for look angles $\theta_p = +43°$ of the total detector FOV. The solar angle $\theta_s$ changes with time of day and with Julian day, and therefore is a precise and predictable natural variable that controls the range of scattering angles $\psi$ through the relation [2].

EXAMPLE 3

CORRECTING THE LOOK ANGLE $\theta_p$ OF A CCD PIXEL ON AN OCEAN PIXEL

The look angle $\theta_p$ of a CCD pixel on the satellite sensor is measured with respect to the zenith direction. However, a correction needs to be applied to this parameter by the relation (see A. Morel, J. L. Mueller, "Normalised Water-Leaving Radiance and Remote Sensing Reflectance: Bi-directional Reflectance and other factors "in Ocean Optics Protocols for satellite Ocean Color Sensor Validation, Rev. 3, Vol 2, pp 183–210, 2002)

$$\theta_p = \theta_{sat} + \sin^{-1}(0.113 \tan \theta_{sat}) \qquad [3]$$

EXAMPLE 4
PROVIDING AN OPERATIONAL FORMULA USED IN CALCULATING THE VOLUME SCATTERING FUNCTION $\beta(\psi,\lambda)$ IN THE BACKWARD DIRECTION AT A GIVEN WAVELENGTH The derivation of the Volume Scattering Function $\beta(\psi,\lambda)$ is based on the definition of water leaving radiance $L(\theta_p)$ which forms the only component of backscattered radiant flux emanating from the ocean surface per unit solid angle per unit projected area. It can be shown that the VSF at a given wavelength is given by the product of the Remote Sensed Reflectance Rrs $(\theta_p,\lambda)$, the diffuse attenuation coefficient Kd, and cosine product of the solar and look angles $(\theta_s,\theta_p)$ respectively Thus $$\beta(\psi,\lambda)=Rrs(\theta_p,\lambda)K_d[\cos\theta_s\cos\theta_p] \quad [4]$$

The relation in [4] is independent of ocean pixel area, CCD pixel element or satellite altitude. Its units in m$^{-1}$.sr$^{-1}$ are that of a scattering function. Rrs is the ratio of the normalized water leaving radiance (nLw) to the mean extra-terrestial solar irradiance at mean earth-sun distance; Kd is the inverse of the satellite penetration depth (m); both quantities obtainable as derived satellite products. The spectral nature of Rrs and Kd makes $\beta(\psi,\lambda)$ a spectral variable also. The angular dependence of the VSF is controlled through the product $[\cos\theta_s\cos\theta_p]$ involving only the solar angle and the look angle. Given the the satellite view angle $\theta_{sat}$, Rrs, Kd, and the solar angle $\theta_s$ at each ocean pixel on a scan line of the satellite swath, it is possible to use the VSF algorithm in [4], and the scattering angle in [2] to calculate a high resolution spatial distribution of the scattering function as a function of scattering angle along a scan line. For a complete swath width this provide 3730 points across the satellite track. The computation can be repeated for subsequent scan lines along the satellite track to reveal a complete 2D scattering distribution of the ocean surface.

Figure 5:
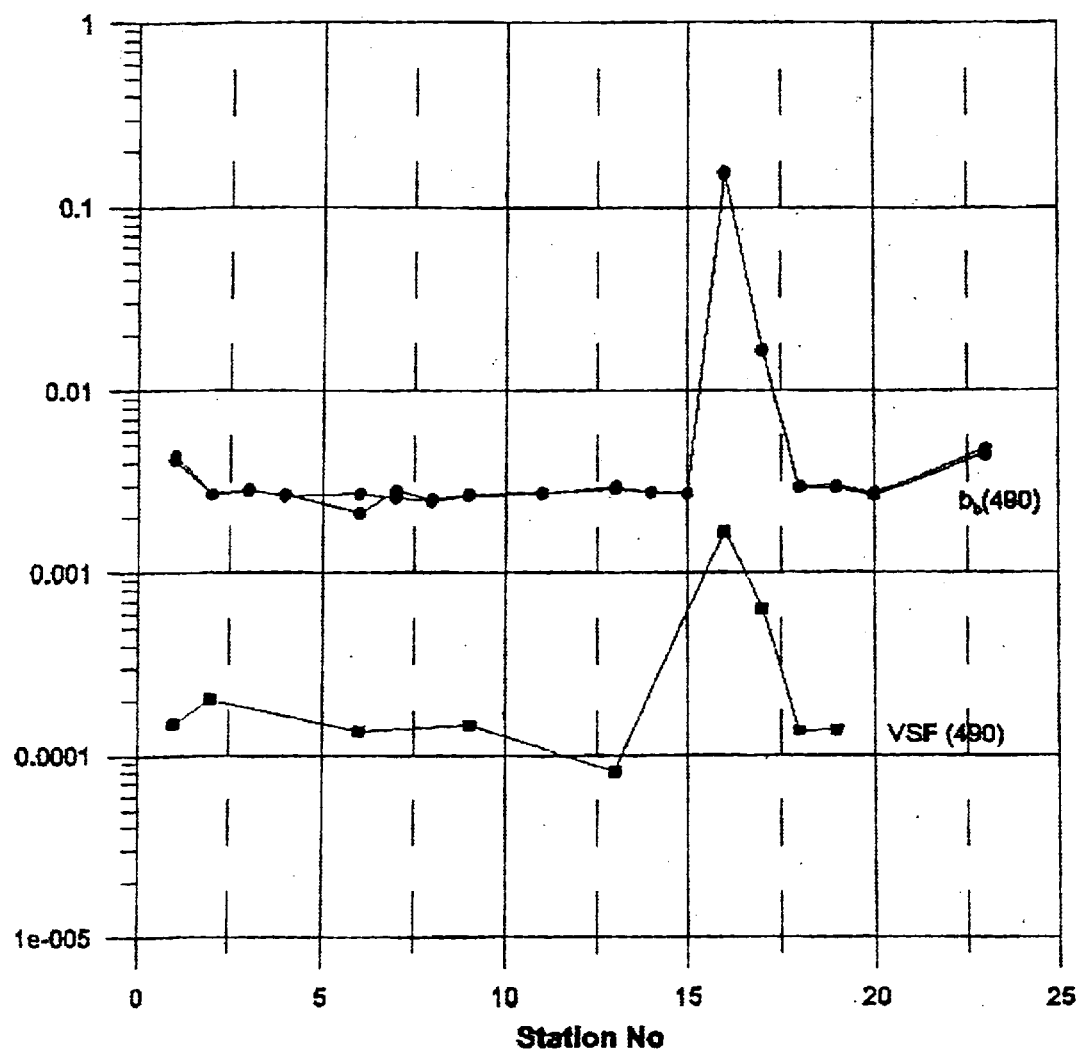
FIG. 5 shows a high resolution variation of the VSF function at 490 nm as a function of the backscattering angle along a scan line of an OCM image of 16 Mar. 2002 where Trichodesmium blooms were viewed in abundance.

EXAMPLE 5
APPLICATION OF THE VSF ALGORITHM IN [4] USING REAL SATELLITE DATA ACROSS A SCAN LINE AT 490 NM WAVEBAND (FIG. 5)

In order to illustrate the novelty of the algorithm in [4], across track satellite pixel data was selected from an OCM image of 16 march 2002 when large patches of Trichodesmium blooms were detected in the coastal waters off the Goa Coast in the Eastern Arabian seaa. This particular dataset consists of all the quantitiesdetailed above and required in the computation of $\beta(\psi,\lambda)$ as a function of the scattering $\psi$. The results are shown in FIG. 5. Moving from the open ocean values of $\beta(\psi, 490)\sim0.0005$ m$^{-1}$.sr$^{-1}$ at scattering angles $\psi=138$ degrees, the VSF shows a steadily increasing value until it encounters the Trichodesmium bloom at $\psi\sim126$ degrees where the scattering angle shows a significant increase to $\beta(\psi, 490)>0.0012$ m$^{-1}$.sr$^{-1}$ near the coast. This simple example for a single scan can be extended for all contiguous scan lines along the satellite track, and for different wavebands so as to map the 2D spectral scattering distribution of the ocean surface.

Figure 6:
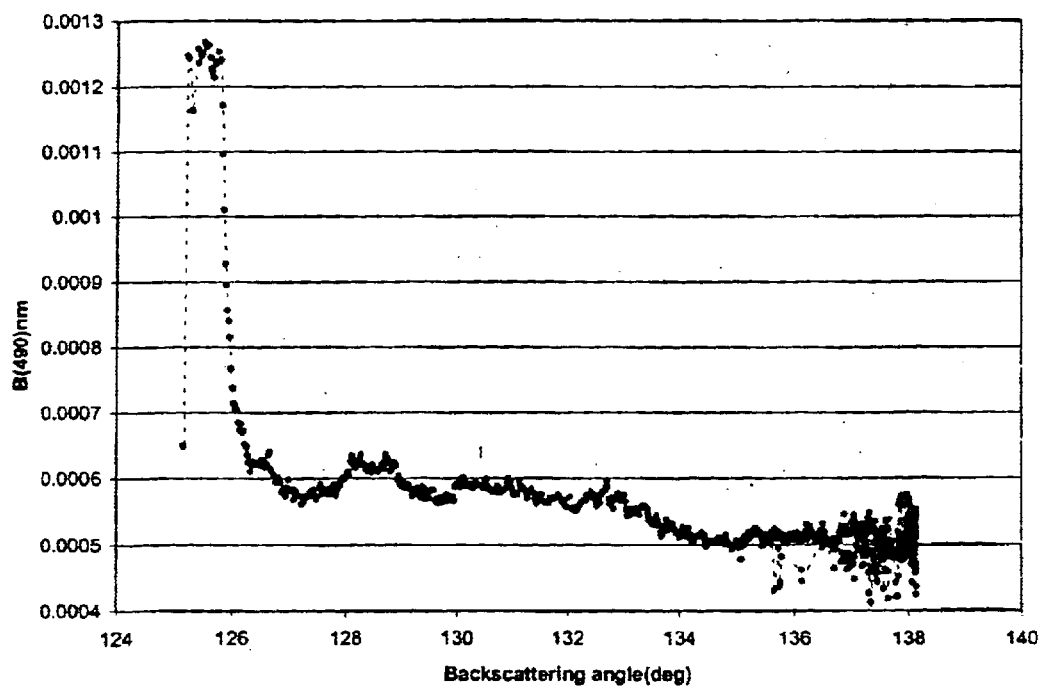
FIG. 6 shows plots (upper) of the backscatter coefficient at 490 nm measured at different stations on a research cruise in November 2001. The corresponding VSF function at 490 nm (lower plot) was computed using SeaWifs data obtained from matched overhead passes at each of the stations.

EXAMPLE 6
COMPARING IN-SITU BACKSCATTER DATA FROM A COMMERCIAL INSTRUMENT WITH THE ALGORITHM IN [4] USING SATELLITE DATA FROM THE SEAWIFS OCEAN COLOR SENSOR (FIG. 6)

The optical backscatter instrument described in the prior art above was used in a recent cruise to the Arabian Sea. This instrument measures the backscatter coefficient at a single backscatter angle. The upper plot in FIG. 6 shows the backscatter coefficient for 18 different stations of the cruise track. At station number 16 the ship encountered dense plumes of sediments in the water resulting in a large backscatter value of $\sim0.1$ ml$^{-1}$.

An independent approach based only satellite data from the SeaWifs Ocean Color sensor was applied using the algorithm of the present invention. Unlike the technology of the OCM sensor on IRS-P4, the SeaWiFs sensor has reduced ocean pixel resolution of 1 km×1 km, and does not employ the push broom technique used in OCM, At each station, SeaWiFs data on Rrs, Kd, $\theta_s$, $\theta_p$ was processed and the VSF algorithm applied to provide the lower plot in FIG. 6. At station 16, the VSF algorithm registered a ten fold increase in the backward volume scattering function exhibiting a significant sensitivity to the presence of sediments in turbid waters.

ADVANTAGES OF THE PRESENT INVENTION

The main advantages of the present invention are:

Provides for a method of determining the backscattered portion of the Volume Scattering Function of oceanic waters by use of a satellite ocean color sensor.

Redefines the concept of a sample volume as that of an ocean pixel 360 meters wide and 250 meters long, and by doing so captures a true representation of suspended particles along large tracts of the ocean.

Extends the method of finding the VSF to eight other spectral wavelengths, and by doing so provides for additional information on the spectral nature of the VSF at ocean scales.

The computation can be repeated for subsequent scan lines along the satellite track to reveal a complete 2D scattering distribution of the ocean surface.

What is claimed is:

1. A method for determining the Volume Scattering Function (VSF) of ocean waters in backward direction using a satellite ocean color sensor, said method comprising the steps of:
   (a) obtaining satellite view angle ($\theta_{sat}$), solar angle ($\theta_s$), remote sensed reflectance [Rrs ($\theta_p,\lambda$)] and diffuse attenuation coefficient (K$_d$) at each ocean pixel on a scaline using a satellite ocean color sensor;
   (b) calculating corrected look angle of a pixel of satellite ocean color sensor on an ocean pixel using:

$\theta_p=\theta_{sat}+\sin^{-1}(0.113\tan\theta_{sat})$; and (c) calculating the Volume Scattering Function of ocean waters in the backward direction at a given wavelength [$\beta(\psi,\lambda)$] using:

$\beta(\psi,\lambda)=Rrs(\theta_p,\lambda)K_d[\cos\theta_s\cos\theta_p]$.

2. A method as claimed in claim 1, wherein the satellite ocean color sensors include CCD array detectors, ocean color monitors and SeaWifs Oocean color sensors.

3. A method as claimed in claim 1, wherein the detectors view a scan line of ocean pixels arranged along a swath of the ocean surface.

4. A method as claimed in claim 1, wherein the swath "W" of the satellite is about 1420 Kms.

5. A method as claimed in claim 1, wherein the about 3730 ocean pixels are covered in a satellite scan line.

6. A method as claimed in claim 1, wherein Instantaneous Field of View (IFOV) of an ocean pixel about 360 meters across track and about 250 meters along track.

7. A method as claimed in claim 1, wherein the Volume Scattering Function of ocean waters in the backward direction is dependent upon the wavelength ($\lambda$).

8. A method as claimed in claim 1, wherein the Volume Scattering Function of ocean waters in the backward direction is obtained at a particular wavelength using appropriate wavelength depenedent products of remote sensed reflectance and diffuse attenuation coefficient.

9. A method as claimed in claim 1, wherein the Volume Scattering Function of ocean waters in the backward direction is obtained at the wavelength of about 490 nm.

10. A method as claimed in claim 1, wherein the method can be extended to contiguous scan lines along the satellite track to generate a high resolution two dimensional volume scattering surface at fixed backscattering angles.

11. A method as claimed in claim 1, wherein the method can be extended to create a set of two dimensional volume scattering surfaces in several different visible bands by the satellite ocean color sensor.

* * * * *